(12) United States Patent
Osborne

(10) Patent No.: US 8,343,204 B2
(45) Date of Patent: Jan. 1, 2013

(54) COMPOSITE STENT GRAFT

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 876 days.

(21) Appl. No.: 12/092,120

(22) PCT Filed: Oct. 31, 2006

(86) PCT No.: PCT/US2006/042402
§ 371 (c)(1), (2), (4) Date: Apr. 30, 2008

(87) PCT Pub. No.: WO2007/053592
PCT Pub. Date: May 10, 2007

(65) Prior Publication Data
US 2008/0288044 A1 Nov. 20, 2008

Related U.S. Application Data

(60) Provisional application No. 60/731,670, filed on Oct. 31, 2005.

(51) Int. Cl.
*A61F 2/06* (2006.01)
(52) U.S. Cl. ...................................... 623/1.11; 623/1.13
(58) Field of Classification Search .................. 623/1.36, 623/1.35, 1.13, 1.15, 1.16, 1.44–1.48, 1.11, 623/1.14
See application file for complete search history.

(56) References Cited

U.S. PATENT DOCUMENTS

| | | | |
|---|---|---|---|
| 4,502,159 A | 3/1985 | Woodroof et al. | |
| 4,675,361 A | 6/1987 | Ward, Jr. | |
| 4,861,830 A | 8/1989 | Ward, Jr. | |
| 4,902,508 A | 2/1990 | Badylak et al. | |
| 5,211,658 A | 5/1993 | Clouse | |
| 5,733,337 A | 3/1998 | Carr, Jr. et al. | |
| 6,129,756 A * | 10/2000 | Kugler et al. | 623/1.27 |
| 6,206,931 B1 * | 3/2001 | Cook et al. | 623/23.75 |
| 6,280,467 B1 | 8/2001 | Leonhardt | |
| 6,331,191 B1 * | 12/2001 | Chobotov | 623/1.44 |
| 6,358,284 B1 | 3/2002 | Fearnot et al. | |
| 6,379,710 B1 | 4/2002 | Badylak | |
| 6,666,892 B2 | 12/2003 | Hiles et al. | |

(Continued)

FOREIGN PATENT DOCUMENTS
WO    WO 98/22158    5/1998
(Continued)

*Primary Examiner* — Kathleen Sonnett
*Assistant Examiner* — Jocelin Tanner
(74) *Attorney, Agent, or Firm* — Brinks Hofer Gilson & Lione

(57) ABSTRACT

A composite prosthesis (19, 99, 199) and method are disclosed herein. This endoluminal prosthesis is constructed by separately deploying a first prosthesis (9, 201) and a second prosthesis (14, 208), wherein the first prosthesis is deployed and secured to the interior surface of a body lumen (260). In a subsequent step, the second prosthesis is deployed substantially within and secured to the first prosthesis. Although additional prostheses may be deployed within the second prosthesis, in a preferred configuration the first and second prostheses combine to provide all of the necessary attributes associated with a functioning endoluminal prosthesis. Thus, one of the first and second prostheses is permeable to blood and exerts sufficient radial force to cause the composite prosthesis to securely engage an interior surface of the body lumen at one or both of the composite prosthesis's proximal and distal ends, while the other of the first and second prostheses is impermeable to blood flow.

26 Claims, 8 Drawing Sheets

U.S. PATENT DOCUMENTS

| | | | |
|---|---|---|---|
| 6,682,557 B1 * | 1/2004 | Quiachon et al. | 623/1.35 |
| 6,685,736 B1 * | 2/2004 | White et al. | 623/1.13 |
| 6,709,455 B1 * | 3/2004 | Chouinard | 623/1.32 |
| 6,986,786 B1 * | 1/2006 | Smith | 623/1.36 |
| 7,244,444 B2 | 7/2007 | Bates | |
| 2001/0049554 A1 | 12/2001 | Ruiz et al. | |
| 2003/0204235 A1 * | 10/2003 | Edens et al. | 623/1.5 |
| 2004/0024443 A1 * | 2/2004 | Dwyer et al. | 623/1.13 |
| 2004/0093068 A1 * | 5/2004 | Bergen et al. | 623/1.15 |
| 2004/0117004 A1 * | 6/2004 | Osborne et al. | 623/1.36 |
| 2005/0131519 A1 | 6/2005 | Hartley | |

FOREIGN PATENT DOCUMENTS

WO     WO 98/53761     12/1998

* cited by examiner

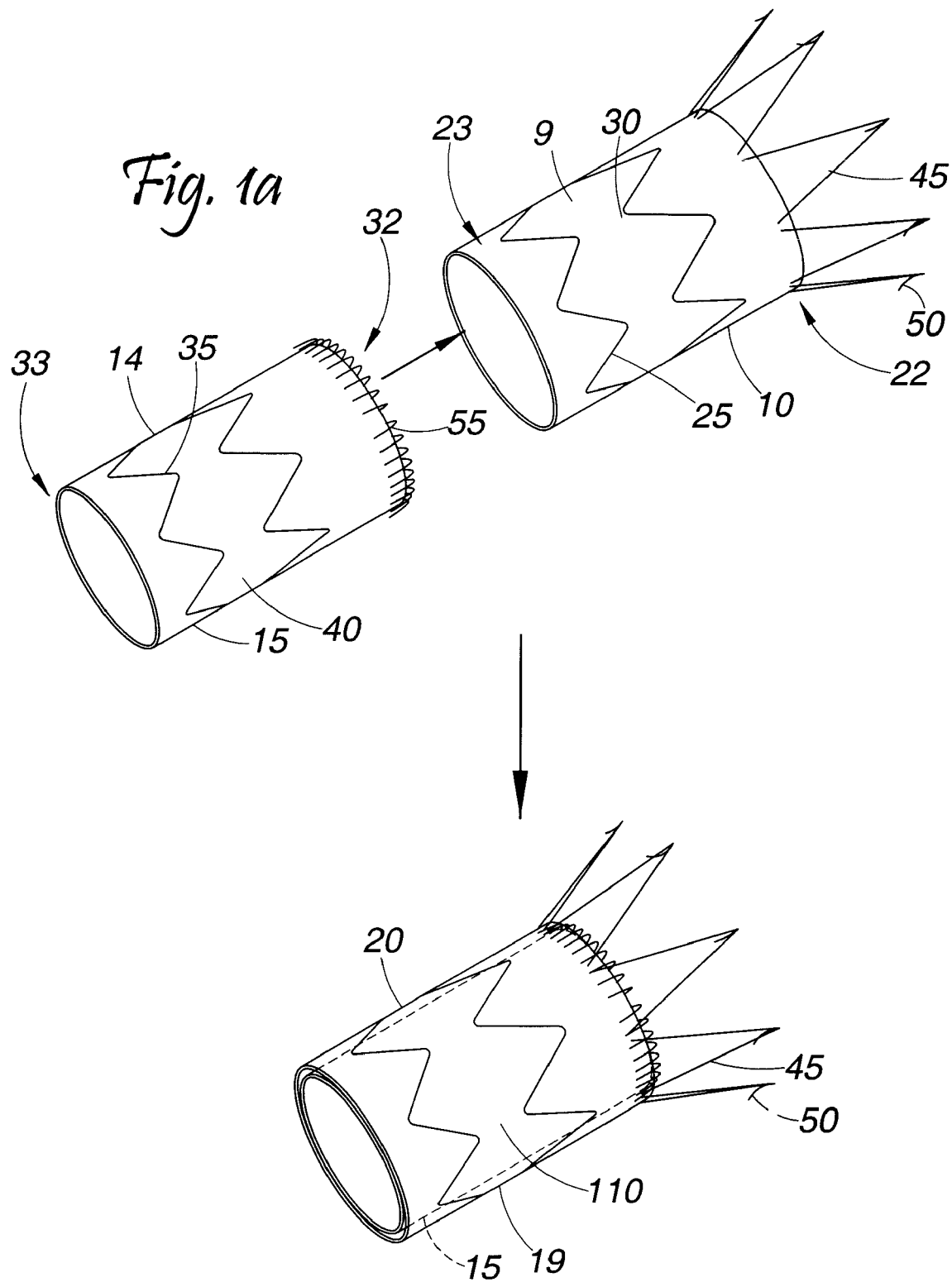

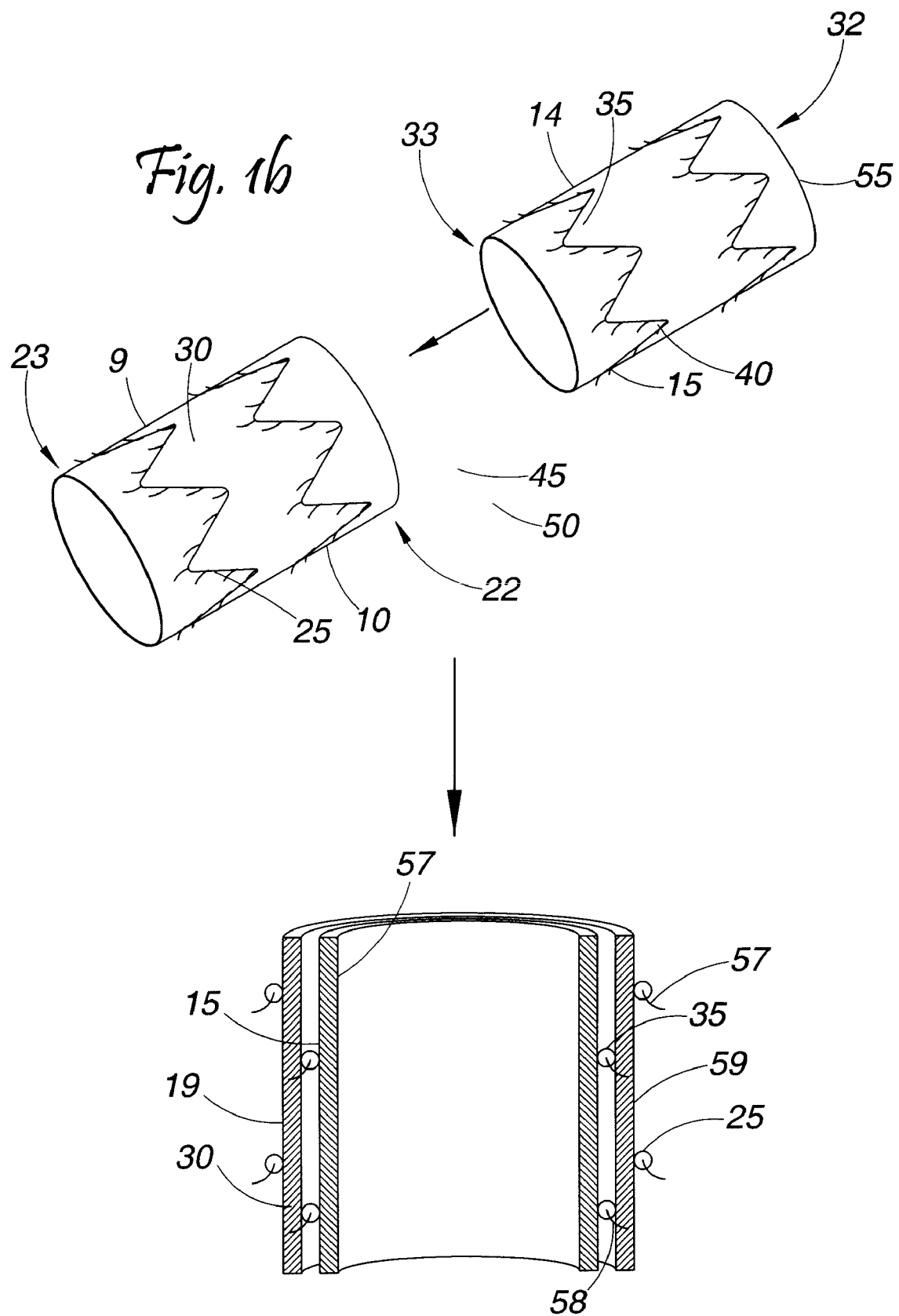

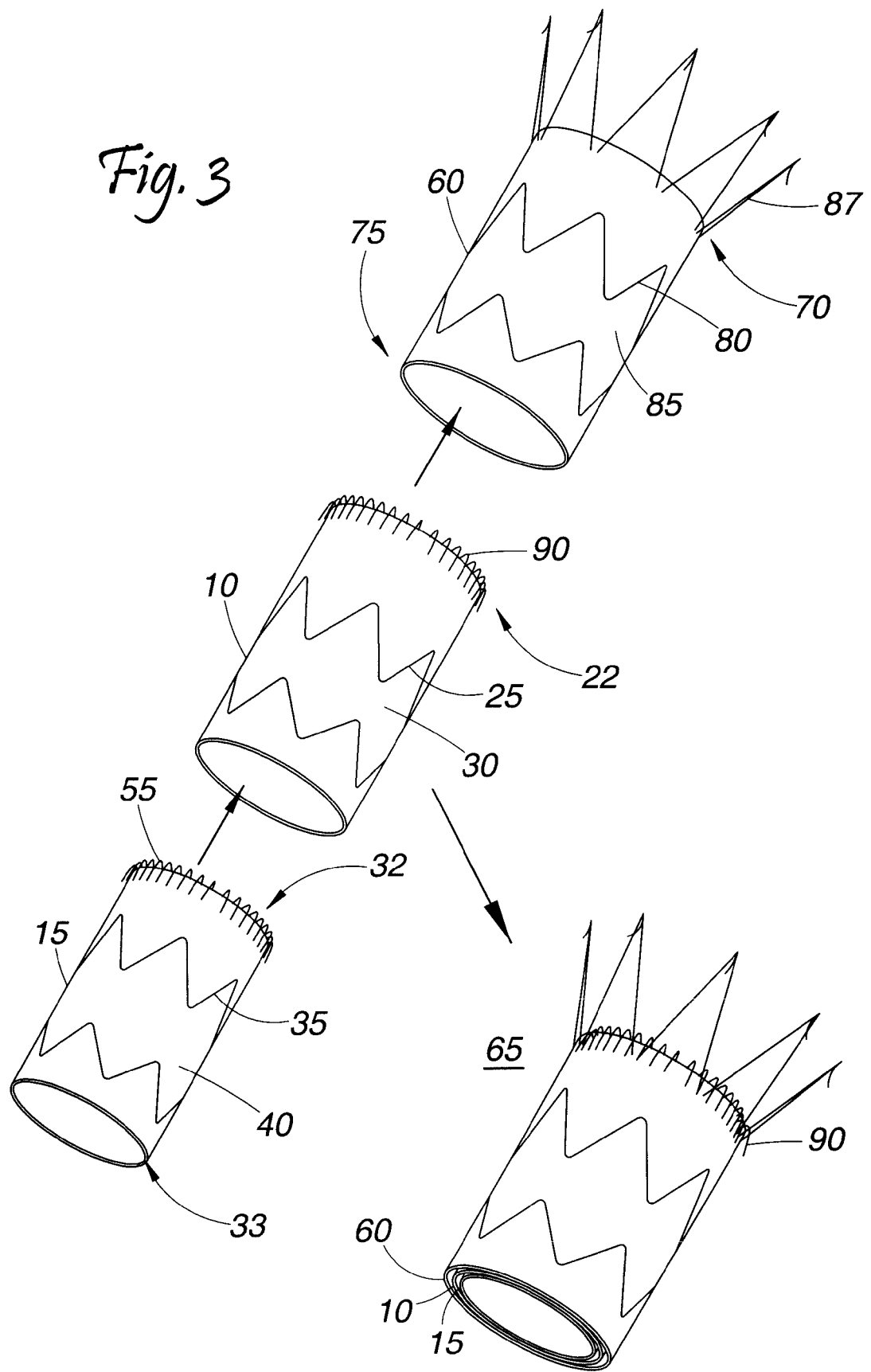

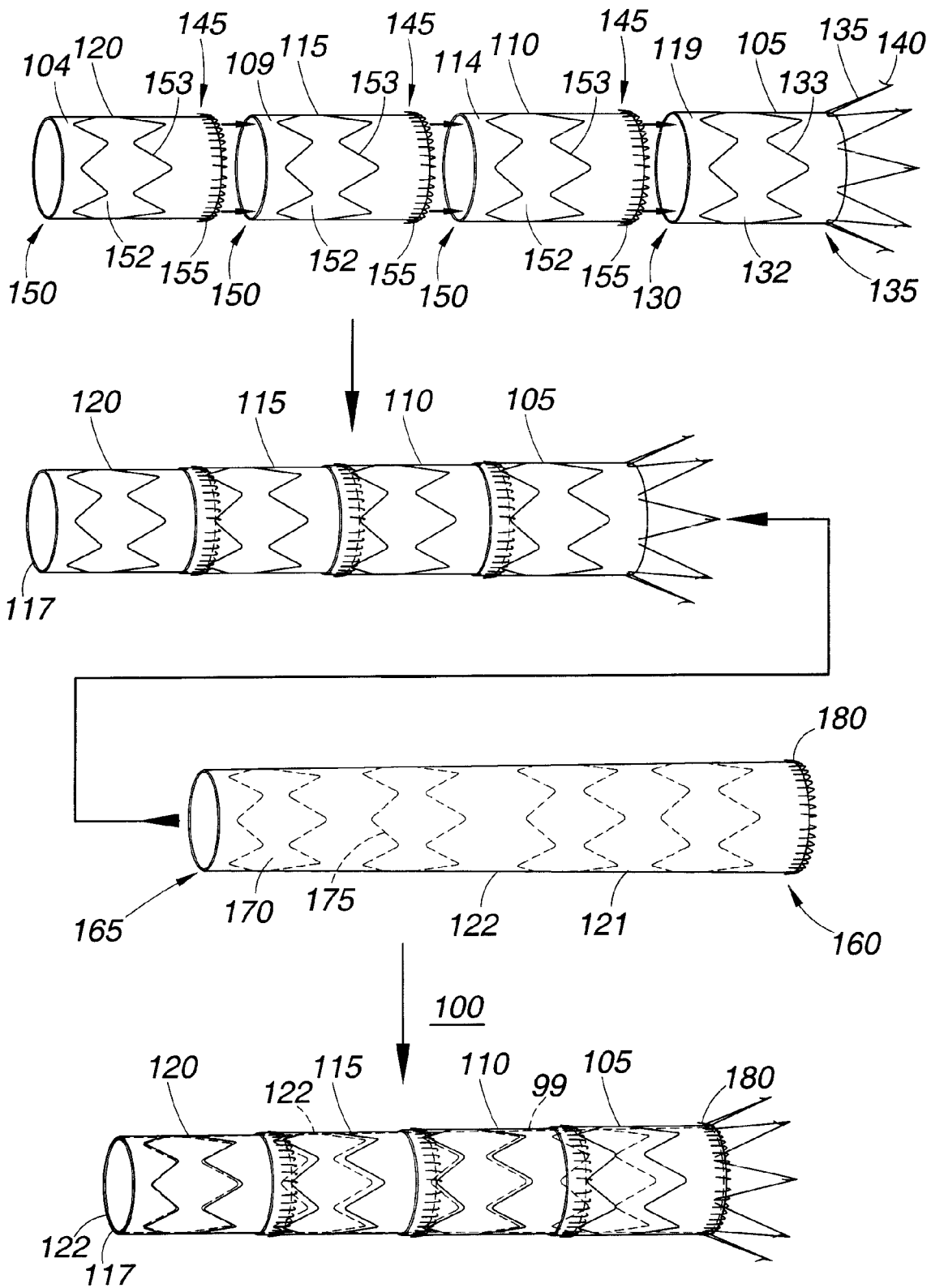

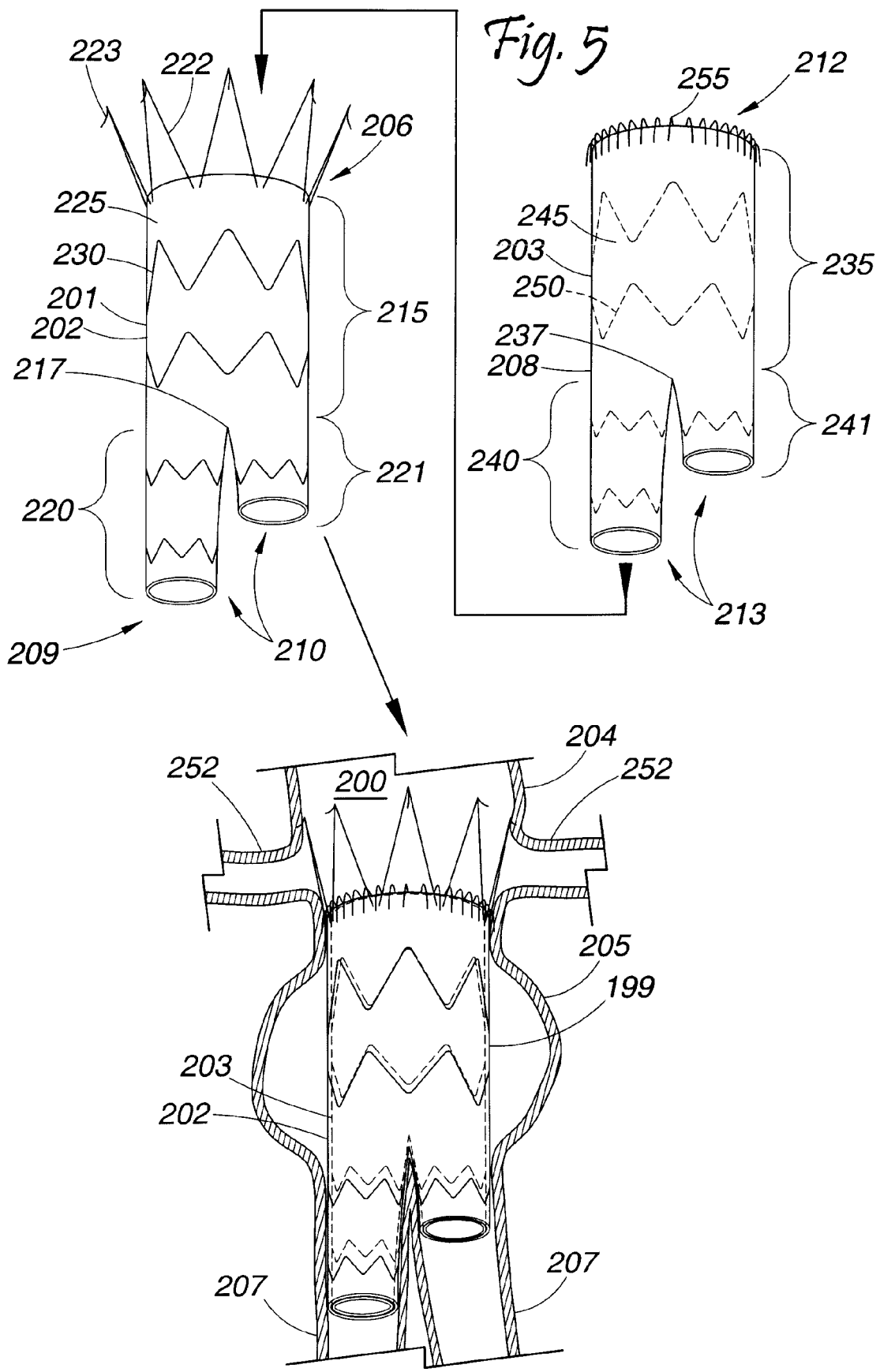

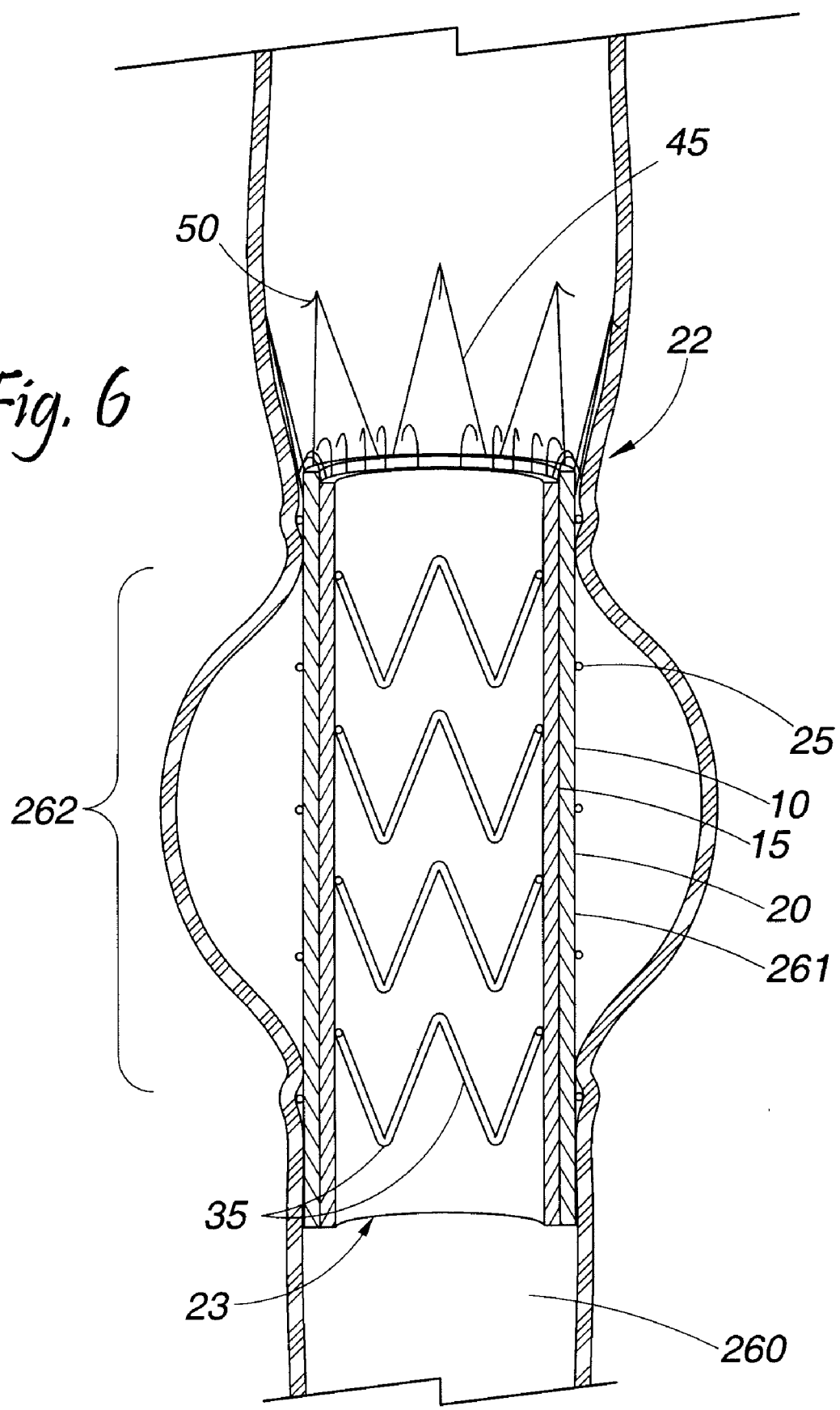

COMPOSITE STENT GRAFT

RELATED APPLICATIONS

The present patent document is §371 filing based on PCT Application Serial No. PCT/US2006/042402, filed Oct. 31, 2006, designating the United States and published in English, which claims the benefit of the filing date under 35 U.S.C. §119(e) of Provisional U.S. Patent Application Ser. No. 60/731,670, filed Oct. 31, 2005. All of the foregoing applications are hereby incorporated by reference.

TECHNICAL FIELD

The present invention relates to composite prostheses for endoluminal placement, in particular composite stent grafts and to methods of deploying such prostheses into a body lumen.

BACKGROUND OF THE INVENTION

The functional vessels of human and animal bodies, such as blood vessels and ducts, occasionally weaken or even rupture. For example, in the aortic artery, the vascular wall can weaken or tear, resulting in dangerous conditions such as aneurysms and dissections. Upon further exposure to hemodynamic forces, such an aneurysm can rupture. In Western European and Australian men who are between 60 and 75 years of age, aortic aneurysms greater than 29 mm in diameter are found in 6.9% of the population, and those greater than 40 mm are present in 1.8% of the population.

One intervention for weakened, aneurysmal or ruptured vessels is the use of an endoluminal device or prosthesis, such as a stent graft, to provide some or all of the functionality of the original, healthy vessel and/or preserve any remaining vascular integrity by replacing a length of the existing vessel wall that contains the site of vessel weakness or failure. Stent grafts for endoluminal deployment are generally formed from a tube of a biocompatible material and one or more stents to maintain a lumen therethrough. Stent grafts effectively exclude the aneurysm by sealing both proximally and distally to the aneurysm, and shunting blood through its length. A device of this type can, for example, treat various arterial aneurysms, including those in the thoracic aorta, abdominal aorta, iliac, or hypogastric artery.

Two closely related aspects of stent graft function are sealing and fixation. The stent graft generally engages the wall of the lumen on both ends of the aneurysm or other defect, at proximal and distal regions referred to as landing or sealing zones. The sealing zones are typically near the termini of the stent grafts. The seal between the stent graft and the vascular wall is typically formed at these locations as a result of the circumferential apposition of the stent graft to the vascular wall. Apposition is typically maintained by the radial force exerted by stents fixed to the stent graft.

It is also desirable to fix, or anchor, the stent graft in place. For example, proximal fixation in the neck region of the aorta is often critical for long term durability of an endoluminal repair using a stent graft. Fixation of the stent graft in part depends on mechanical anchoring mechanisms. For example, in one anchoring mechanism the frictional forces between the stent graft and aortic wall may be generated by an interference fit created between the stent graft and aorta wall. The frictional forces may be supported by an underlying stent or stents. The practice of over-sizing a device for the lumen into which it is to be placed may also increase these frictional forces. Fixation may also be assisted by small hooks or barbs that extend from the stent graft and penetrate the arterial wall. In both cases, fixation is immediate and does not require long term biological interaction. In contrast, tissue encapsulation may also occur in some devices over a longer time frame. Exposed stainless steel stent struts and other parts of the stent graft may eventually become completely encapsulated by tissue growth, thereby assisting fixation.

One example of an endoluminal device, is a bifurcated stent graft, which is known for use in treating abdominal aortic aneurysms. The proximal end of the bifurcated stent graft defines a single lumen for placement within the aorta, while the distal end of the bifurcated stent graft defines a bifurcated region that encompasses two lumens. One such stent graft is disclosed in PCT application WO98/53761 and is useful for repair of abdominal aortic aneurysms. That application discloses a stent graft that includes a sleeve or tube of biocompatible graft material, such as woven polyester fabric or polytetrafluoroethylene (PTFE), defining a main lumen and two iliac limbs, where the graft material is impermeable to blood flow. The stent graft also includes several stents secured therealong. The stent graft is designed to span an aneurysm that extends along the aorta between the iliac and renal arteries.

In the WO98/53761 application, the fabric-covered portion of the single-lumen proximal end of the stent graft bears against the wall of the aorta above the aneurysm and distal to the renal arteries to seal off the aneurysm. Thin wire struts of a juxtarenal attachment stent or anchoring stent traverse the renal artery ostia without occluding them. Barbs on the anchoring stent then help to anchor the stent graft in place.

One bifurcated stent graft approved by the Food and Drug Administration (FDA) to treat aortic aneurysms is the ZENITH® AAA Endovascular Graft (Cook Incorporated, Bloomington, Ind.). The ZENITH® AAA Endovascular Graft is made up of three prosthetic modules: a bifurcated main body module and two leg modules. The main body is positioned in the aorta. The legs are positioned in the iliac arteries and connect to the main body. The stent graft thus extends from a section of the aorta, usually below the renal arteries, and into both iliac arteries. The graft material is made of a woven polyester fabric like that used in open surgical repair. Standard surgical suturing techniques are used to sew the graft material to a frame of stainless steel stents. These self-expanding stents provide support for the graft material.

In a conventional stent graft, the graft material must be extremely strong, wear resistant and substantially impermeable to liquids, such that it provides a barrier to blood flow. This combination of attributes generally necessitates a thick or bulky graft material. For example, one commonly utilized graft material possessing these attributes is tightly woven polyester, which has a thickness of about 0.2 to 0.3 mm. Adding to the bulk of a typical stent graft device are a plurality of sutures, which are typically employed to attach the graft material to the stent(s) of the stent graft device.

Unfortunately, in order to achieve the aspects of stent graft function described above, the combination of the stent, the graft material and the sutures results in a prosthesis with a bulk that can limit the compressibility of the prosthesis. Consequently, delivery of conventional stent grafts may require a larger than preferred diameter delivery sheath, making delivery of the stent graft via percutaneous entry into the femoral artery, for example, infeasible. In addition, the larger the diameter of the delivery sheath and the bulk of the enclosed stent graft may limit the flexibility during endoluminal placement.

Accordingly, the present invention seeks to overcome at least one of these disadvantages.

SUMMARY OF THE INVENTION

In one aspect of the invention, there is a composite prosthesis that includes a first prosthesis for endoluminal placement within a body lumen and a second prosthesis for subsequent endoluminal placement within the first prosthesis. One of the first and second prostheses is permeable to blood and exerts sufficient radial force to cause the composite prosthesis to securely engage an interior surface of the body lumen at one or both of the composite prosthesis's proximal and distal ends, while the other of the first and second prostheses is impermeable to blood flow. An advantage of this arrangement is that since the individual prostheses do not have all of the attributes of a fully functional stent graft, they can be more highly compressed for delivery. Thus percutaneous introduction is possible.

In another aspect of the invention, there is a composite prosthesis that includes a first prosthesis for endoluminal placement within a body lumen and a second prosthesis for subsequent endoluminal placement within the first prosthesis. In this aspect of the invention, the first prosthesis is an outer stent graft, the second prosthesis is an inner stent graft and the composite prosthesis is a composite stent graft. In addition, the outer stent graft is permeable to blood and exerts sufficient radial force to cause the composite stent graft to securely engage an interior surface of the body lumen at one or both of the composite stent graft's proximal and distal ends. The inner stent graft, on the other hand, is impermeable to blood flow. Also in this aspect of the invention, the inner stent graft exerts sufficient radial force to engage the outer stent graft.

In a further aspect of the invention, there is a composite stent graft comprising an outer stent graft and an inner stent graft for subsequent endoluminal placement within the outer stent graft. The outer stent graft comprises at least one outer stent and an outer graft. The at least one outer stent has a radial force sufficient to securely engage an interior surface of a body lumen at one or both of the outer stent graft's proximal and distal ends, while the outer graft is permeable to blood. The outer stent graft further comprises a plurality of anchoring stents with barbs, wherein the anchoring stents are attached to and extend proximally from the proximal end of the outer graft. The inner stent comprises at least one inner stent, an inner graft and a plurality of anchoring hooks. The at least one inner stent exerts sufficient radial force to engage the outer stent graft, while the inner graft is impermeable to blood. The plurality of anchoring hooks are attached to and extend proximally from the inner graft and the anchoring hooks engage the proximal end of the outer stent graft.

In yet another aspect of the invention, there is provided a method of deploying a composite prosthesis into a body lumen that includes endoluminally deploying a first prosthesis within a body lumen and then endoluminally deploying a second prosthesis within the first prosthesis. One of the first and second prostheses is permeable to blood and exerts sufficient radial force to cause the composite prosthesis to securely engage an interior surface of the body lumen at one or both of the composite prosthesis's proximal and distal ends, while the other of the first and second prostheses is impermeable to blood flow. In a further aspect of the invention, the first prosthesis is an outer stent graft, the second prosthesis is an inner stent graft and the composite prosthesis is a composite stent graft.

BRIEF DESCRIPTION OF THE DRAWING

Preferred embodiments of the invention will now be described by way of example only and with reference to the drawings in which:

FIG. 1a shows a first prosthesis, a second prosthesis and a composite prosthesis FIG. 1b shows a first prosthesis, a second prosthesis and a composite prosthesis;

FIG. 3 shows an outer stent graft and an inner stent graft, wherein the outer stent graft and the inner stent graft are deployed within a tertiary stent graft;

FIG. 4 shows a plurality of first prostheses combined with a second prosthesis to provide a telescoping composite prosthesis;

FIG. 5 shows a first prosthesis and a second prosthesis, which are combined within an abdominal aortic aneurysm to provide a composite bifurcated prosthesis;

FIG. 6 shows a cross-sectional view of a composite prosthesis deployed within a lumen and spanning an aneurismal region.

DETAILED DESCRIPTION

Figure 2A:
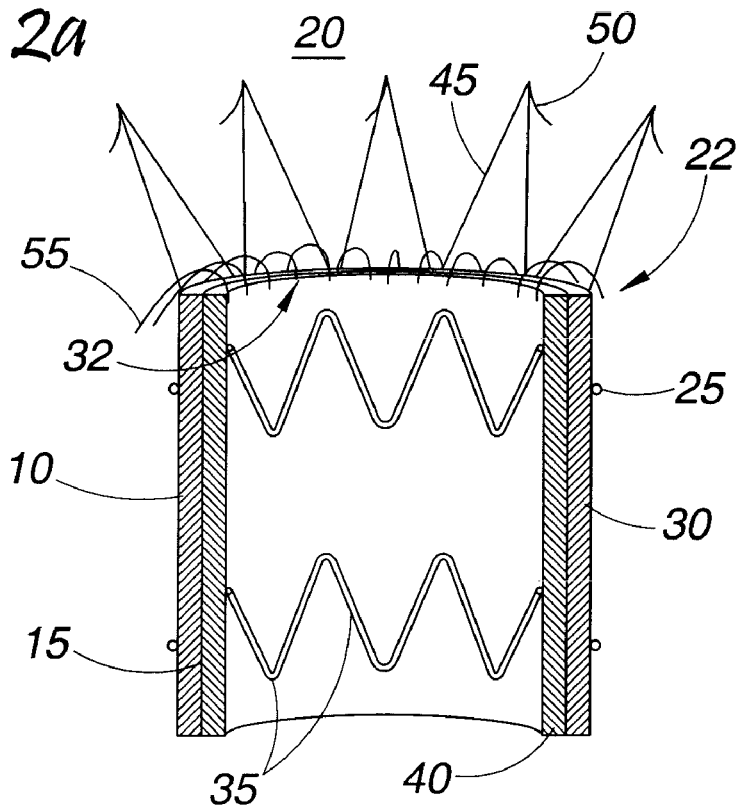
FIG. 2a shows a cross-sectional view of a composite stent graft comprising an inner stent graft and an outer stent graft.

The present invention relates to an endoluminal prosthesis that may be used, for example, to treat an aneurysm. Typically, treatment of an aneurysm focuses on preventing blood from flowing into an aneurysm, thereby decreasing the blood pressure that is present within the aneurysm. Treatment is sometimes achieved using a stent graft that is composed of a tubular graft material, which is impermeable to blood flow, in combination with at least one stent. A typical stent graft functions by securing the graft material to the patient's blood vessel before and after the aneurysm, such that it forms a seal against the interior surface of the patient's blood vessel at both of these locations, thus directing blood flow through the stent graft. These devices are generally introduced by a delivery catheter or introducer, where the delivery catheter contains a compressed configuration of the stent graft. After the delivery catheter is directed through the patient's blood vessel to the aneurysm, the stent graft is expelled from the catheter and is converted to an expanded configuration that is secured to the patient's blood vessel.

The endoluminal prosthesis of the present invention is constructed by separately deploying a plurality of prostheses within a patient, where a first prosthesis is deployed and is secured to the interior surface of a body lumen. Next, a second prosthesis is deployed substantially within and secured to the first prosthesis. Although additional prostheses may be deployed within the second prosthesis, in a preferred configuration the inner and outer prostheses combine to provide all of the necessary attributes that are essential for a functioning endoluminal prosthesis, as is used to treat an aneurysm. For example, one of these prostheses may act as a blood impermeable barrier, while the other prosthesis may serve to provide the radial support that is necessary to secure and seal the blood impermeable prosthesis against the interior surface of the patient's body lumen.

The present invention thus separates the necessary characteristics of a typical stent graft into a plurality of prostheses that are separately delivered. Since the individual prostheses of the present invention do not have all of the attributes of a fully functional stent graft, they may be capable of being more highly compressed for delivery. Thus, the outer prosthesis and the inner prosthesis are preferably loaded into delivery catheters having smaller diameters and greater flexibilities than those for typical stent grafts. As a result, these prostheses may be introduced into the patient via percutaneous techniques and may be more easily guided through the patient's blood vessels. However, once the inner and outer prostheses are implanted, they are designed to form a composite prosthesis that provides a secure attachment to the body lumen and the requisite blood impermeability and sealing.

In one embodiment, the first prosthesis comprises an outer stent graft and the second prosthesis comprises an inner stent graft. The outer stent graft is deployed and anchored within a body lumen. In a subsequent step, the inner stent graft is deployed substantially within and attached to the outer stent graft, such that the outer and inner stent grafts are substantially co-axial. In this embodiment, the outer stent graft has a radial force sufficient to keep it securely against the inner surface of the body lumen at the proximal end, the distal end or both. However, the outer stent graft is preferably relatively thin-walled and is thus permeable to blood flow. In contrast, the inner stent graft preferably does not exert the same level of radial force, but is, nevertheless, impermeable barrier to blood flow. Thus the outer stent graft and the inner stent graft are designed to provide a functioning composite stent graft once they are combined. This strategy provides outer and inner stent grafts having reduced collapsed sizes and greater flexibilities, relative to conventional stent grafts.

Throughout this specification, when discussing the application of this invention to the aorta, the term distal with respect to a prosthesis is intended to refer to the end of the prosthesis furthest away in the direction of blood flow from the heart, and the term proximal is intended to mean the end of the prosthesis that, when implanted, would be nearest to the heart.

The term "impermeable" refers to an amount of blood that will pass through a barrier, such as a graft material, where the amount of blood that will pass through an impermeable barrier is less than the amount of blood that would be deleterious to a patient.

The term "permeable" refers to an amount of blood that will pass through a barrier, such as a graft material, where the amount of blood that will pass through a permeable barrier is equal to or more than the amount of blood that would be deleterious to a patient.

The term "prosthesis" means any replacement for a body part or for a function of that body part; or any device that enhances or adds functionality to a physiological system.

The term "endoluminal" describes objects that are found or can be placed inside a lumen or space in the human or animal body. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The term "graft" means a generally cannular or tubular member which acts as an artificial vessel. A graft by itself or with the addition of other elements can be an endoluminal prosthesis.

The term "stent" means any device or structure that adds rigidity, expansion force or support to a prosthesis. Stents may have a wide variety of configurations and may be balloon-expandable or self-expanding. Generally, stents have a circular cross-section when fully expanded, so as to conform to the generally circular cross-section of a body lumen. For example, the stents used in the stent graft sections may be discrete stents having a zig-zag configuration in which struts are set at angles to each other and are connected by acute bends. The struts are thus connected into an endless loop, forming a generally tubular structure. Discrete zig-zag stents are also referred to as Gianturco stents or Z-stents.

Stents, including anchoring stents, may be made of any rigid biocompatible material, such as metal, plastic or ceramic. Preferably the stents are made of a metal, such as stainless steel, nitinol, and other biocompatible alloys. Stents may be equipped with one or more barbs to secure the prosthesis to the vessel wall or to another component of the prosthesis. If the stent is secured to the graft material by suturing, the sutures may be positioned along struts and/or at bends within the stent. For stents having a zig-zag configuration, it may be desirable to employ two sutures at each bend of the stent to further increase the stability of the connection, as described in Australian Provisional Patent Application No. 2002950951, which is incorporated herein by reference.

"Biocompatible" describes something that can be substantially non-toxic in the in vivo environment of its intended use, and is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse reaction or response. Furthermore, biocompatibility can be affected by other contaminants such as prions, surfactants, oligonucleotides, and other agents or contaminants.

"Extracellular matrix" (ECM) is a collagen-rich substance that is found in between cells in animal tissue and serves as a structural element in tissues. It is generally a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, dura mater, liver basement membrane, pericardium or other tissues.

"Tela submucosa" or "submucosa" refers to a layer of collagen-containing connective tissue occurring under the mucosa in most parts of the alimentary, respiratory, urinary and genital tracts of animals. Tela submucosa is a preferred source of ECMM.

Upon implantation into a host, ECMM may undergo remodeling and induce the growth of endogenous tissues. When implanted, ECMM may be able to serve as a matrix for, promote and/or induce the growth of endogenous tissue and undergo a process of bioremodeling. Common events related to this bioremodeling process may include: widespread and rapid neovascularization, proliferation of granulation mesenchymal cells, biodegradation/resorption of implanted purified intestinal submucosa material, and lack of immune rejection.

Studies have shown that warm-blooded vertebrate submucosa may be capable of inducing host tissue proliferation, bioremodeling and regeneration of tissue structures following implantation in a number of in vivo microenvironments including lower urinary tract, body wall, tendon, ligament, bone, cardiovascular tissues and the central nervous system.

Upon implantation, cellular infiltration and a rapid neovascularization may be observed and the submucosa material may be bioremodeled into host replacement tissue with site-specific structural and functional properties. This may occur as a result of one or more of the components of submucosa including, for example, glycosaminoglycans, glycoproteins, proteoglycans, and/or growth factors, including Transforming Growth Factor-α, Transforming Growth Factor-β, and/or Fibroblast Growth Factor 2 (basic).

ECMM is preferably obtained from human or other mammalian sources, including animals raised for meat production, e.g., pigs, cattle and sheep or other warm-blooded vertebrates. More specifically, ECMM is preferably made from a submucosa isolated from the alimentary, respiratory, urinary or genital tracts, renal capsule or other appropriate sources. In general, purified submucosa is prepared from these tissue sources by delaminating the purified submucosa from both the smooth muscle layers and the mucosal layers. The preparation of intestinal submucosa is described in U.S. Pat. No. 4,902,508, and the preparation of tela submucosa is described in U.S. Pat. No. 6,206,931 (U.S. patent application Ser. No. 08/916,4901, both of which are incorporated herein by reference. The preparation of submucosa is also described in U.S. Pat. No. 5,733,337 and in 17 Nature Biotechnology 1083 (Nov. 1999); and WIPO Publication WO 98/22158, dated 28 May 1998, which is the published application of PCT/US97/14855.

Purified tela submucosa, a preferred type of ECMM, has been previously described in U.S. Pat. Nos. 6,206,931, 6,358, 284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference.

FIG. 1a shows a first prosthesis 9, a second prosthesis 14 and a composite prosthesis 19. In this embodiment, the first prosthesis 9 is an outer stent graft 10 that extends between an outer proximal end 22 and an outer distal end 23, wherein the outer stent graft 10 comprises at least one outer stent 25 and an outer graft 30. The second prosthesis 14 comprises an inner stent graft 15 that extends between an inner proximal end 32 and an inner distal end 33, wherein the inner stent graft 15 comprises at least one inner stent 35 and an inner graft 40. Also in this embodiment, the composite prosthesis 19 is a composite stent graft 20.

The outer stent graft 10 and the inner stent graft 15 can be converted from a compressed configuration to an expanded configuration, wherein the outer stent graft 10 and the inner stent graft 15 can be self-expanding or balloon expandable. However, the outer stent graft 10 and the inner stent graft 15 are preferably self-expanding. The outer stent graft 10 has a radial force that is sufficient to keep the outer stent graft 10 fitted securely against the surface of a body lumen at the outer proximal end 22, the outer distal end 23 or both. In addition, the outer stent graft 10 is permeable to blood flow. Permitting the outer stent graft 10 to be permeable to blood flow allows the use of a thinner outer graft 30, which concomitantly provides the outer stent graft 10 with enhanced compressibility relative to a typical stent graft. This can also provide the outer stent graft 10 with enhanced flexibility. Conversely, the inner stent graft 15 is impermeable to blood flow, but the inner stent graft 15 preferably exerts less radial force than that exerted by the outer stent graft 10. Although the inner graft 40 must be impervious to blood flow, it does not have to be resistant to abrasion since, in this embodiment, it does not constitute the outer surface of the composite stent graft 20. In this embodiment, the radial force exerted by the inner stent graft 15 is not be sufficient to assist in keeping the outer stent graft 10 fitted securely against the surface of the body lumen, but it should be sufficient to expand the inner graft material 35, such that the inner stent graft 15 is kept securely against the outer stent graft 10. Use of an inner stent 35 with a lower radial force and use of a graft material that does not have to be abrasion resistant provides the inner stent graft 15 with enhanced compressibility and flexibility relative to a typical stent graft. Due to the enhanced compressibility of the outer stent graft 10 and the inner stent graft 15, each of these are preferably loaded into and deployed using delivery catheters with smaller diameters and greater flexibility than those used for typical stent grafts.

In one embodiment, the collapsed size of the stent grafts 10 and 15 may be further reduced by making the stents 25 and 35 from a wire with a rectangular cross section, where the short side of the rectangle is perpendicular to the circumference of the stent graft. Employing a rectangular wire for the stents 25 and 35 should also provides a smoother bore in the compressed stent.

The composite stent graft 20 results from the initial deployment of the outer stent graft 10 within the body lumen, followed by a subsequent and separate insertion of the inner stent graft 15 into the outer stent graft 10. The enhanced compressibility of the stent grafts 10 and 15 allows for each of these to be delivered via percutaneous entry into a patients body lumen.

The grafts 30 and 40 comprise a biocompatible graft material, which may be in the form of a fabric. Graft materials may include biocompatible polymers. Examples of biocompatible polymers include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer may be used to make a graft material, provided the final material is biocompatible.

Examples of biocompatible polyurethanes include THORALON (THORATEC, Pleasanton, Calif.), BIOSPAN, BIONATE, ELASTHANE, PURSIL and CARBOSIL (POLYMER TECHNOLOGY GROUP, Berkeley, Calif.). As described in U.S. Patent Application Publication No. 2002/0065552 A1, incorporated herein by reference, THORALON is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A porous polymeric sheet can be formed from these two components by dissolving the base polymer and additive in a solvent such as dimethylacetamide (DMAC) and solidifying the mixture by solvent casting or by coagulation in a liquid that is a non-solvent for the base polymer and additive.

Examples of biocompatible polyesters include DACRON® (DUPONT, Wilmington, Del.) and TWILL-WEAVE® MICREL (VASCUTEK, Renfrewshire, Scotland).

Another potential biocompatible graft material is ECMM, such as a purified collagen-based matrix derived from submucosa tissue. A specific example of an ECMM is small intestinal submucosa (SIS), such as is described in U.S. Pat. No. 6,206,931, which is incorporated herein by reference. In a further embodiments, the grafts 30 and 40 may comprise a porous biocompatible polymer in which a collagenous biomaterial has been dispersed, as is disclosed in U.S. Provisional Application Ser. No. 60/558,794 filed Mar. 31, 2004 and U.S. Provisional Application Ser. No. 60/558,667 filed Mar. 31, 2004 (both now U.S. Pat. No. 7,244,444), which are hereby incorporated herein by reference.

The grafts 30 and 40 may be made of a single material, or may be a blend, weave, laminate or composite of two or more materials. The graft material may also include other additives, such as plasticizers, compatibilizers, surface modifiers, biological materials such as peptides and enzymes, and therapeutic agents such as drugs or other medicaments.

In order to achieve enhanced collapsibility for the inner stent graft 15 and the outer stent graft 10, the material from which the grafts 30 and 40 are produced should be selected based on the material's ability to achieve an enhanced collapsibility. Furthermore, the biocompatible graft materials selected for grafts 30 and 40 may be the same or different. For example, when the graft materials are different, the graft 30 may comprise a loosely woven, fine denier polyester, while the graft 40 may comprise an impermeable PTFE.

In a preferred embodiment, the outer graft 30 may consist of loosely woven, fine denier polyester. The loosely woven, fine denier polyester although permeable to blood flow, will preferably provide resistance to abrasion and a thickness of about 0.1 mm. In another preferred embodiment, the outer stent 25 may be incorporated into the weave of the loosely woven, fine denier polyester graft 30 (See FIG. 2b). This should provide a smooth walled outer stent graft 10 with enhanced compressibility. The inner graft 40 may consist of a flexible, blood impermeable and biocompatible polymeric film. Suitable films, for example, may include both cross-linked and non-cross-linked polytetrafluoroethylene (PTFE) and polyethylene, Other suitable films, for example, may also include: silicone rubber; thermoset materials; and biocompatible polyurethane elastomers, such as Carbothane® from Noveon, Inc. and Tecoflex®. In addition, Thoralon® may also serve as a biocompatible polymeric film. In one preferred embodiment, the inner stent 35 could be incorporated directly into the inner graft 40, where the graft material comprises a polymeric film. For example, a solution of the polymeric film may be cast directly around the stent.

In this embodiment, the outer stent graft 10 is equipped with a plurality of proximal anchoring stents 45 that are attached to and extend proximally from the outer graft 30 near the outer proximal end 22. In a preferred embodiment, the anchoring stents 45 are delivered in a compressed state and are self-expanding. The proximal anchoring stents 45 include barbs 50 to provide for anchoring of the composite stent graft 20 proximal to the aneurysm. Thus once the outer stent graft 10 is deployed within the desired body lumen, the anchoring stents 45 are expanded such that the barbs 50 engage the tissue of the body lumen, securing the outer stent 10 within the body lumen. The proximal anchoring stents 45 may be secured to the interior and/or the exterior of the outer graft material 30 and the proximal anchoring stents 45 may be secured by sutures.

When the grafts 30 and 40 are attached to the stents 25, 35, and 30 by sutures, the sutures may be made of any biocompatible fiber suitable for the application, including but not limited to, monofilament or braided multi-filament polyester, nylon, polyaramid, polypropylene, and polyethylene. Braided polyester 4-0 suture material is preferred for attaching internal stents to grafts, while monofilament suture material is preferred for attaching top stents to grafts. The polyester 4-0 suture material is non-absorbable and has limits of 0.150 to 0.199 mm (metric size 1.5). This well-known material is commercially available from a number of companies. The suture material may be attached to a hollow needle used to thread the suture through the graft, thus attaching the stent to the graft using any suitable type of knot. It is not necessary to the invention that fiber suture be used to attach the supporting structure to the graft material. Wire, staples, clips, bonding agents, or other methods also may be used to achieve a secure attachment of the graft material and stents.

In this embodiment, the inner stent graft 15 is equipped with a plurality of inner anchoring hooks 55 that are attached to and extend from the inner graft material 35. The inner anchoring hooks 55 are located near the inner proximal end 32 and may be secured to the graft material 40 in any suitable manner. For example the inner anchoring hooks 55 may be secured by sutures or may be woven into the graft material. The anchoring hooks 55 may be made of any rigid biocompatible material, such as metal, plastic or ceramic. Preferably the anchoring hooks 55 are made of a metal, such as stainless steel, nitinol, and other biocompatible alloys.

When the inner stent graft 15 is deployed within the outer stent graft 10, the anchoring hooks 55 should engage the outer stent graft 10, thus securing the inner stent graft 15 to the outer stent graft 10. In a preferred embodiment, the inner anchoring hooks 55 engage the outer proximal end 22 of the outer stent graft 10. A variety of other techniques may be used to secure the inner stent graft 15 to the outer stent graft 10 (for example See FIG. 1b).

The dimensions of the outer stent graft 10 and the inner stent graft 15 are determined by the intended use of the prosthesis. Ideally, the stent grafts 10 and 15 are constructed so as to provide the optimum fit of the prosthesis assembly within the vasculature to be treated. The dimensions of the vasculature may be determined by a variety of methods, including intraoperative intravascular ultrasound (IVUS) and radiologic studies such as computerized tomography (CT), magnetic resonance imaging (MRI), angiography.

In another embodiment, the first prosthesis 10 supplies the requisite impermeability, while the second prosthesis 15 is permeable to blood, but exerts sufficient radial force to cause the composite prosthesis 19 to securely engage an interior surface of the body lumen at one or both of the composite prosthesis's proximal and distal ends.

FIG. 1b shows the first prosthesis 9, the second prosthesis 14 and a cross-sectional view of a composite prosthesis 19. In this embodiment, these correspond to the outer stent graft 10, the inner stent graft 15 and a composite stent graft 59, respectively. In this embodiment, the outer stent graft 10 does not have anchoring stents 45, but is secured to the surface of the body lumen via a plurality of outer anchoring barbs 57. The outer anchoring barbs 57 are attached to and extend from the outer stents 25. In one embodiment, the barbs 57 may be located on all of the outer stents 25 and in another embodiment, the barbs 57 may be located on only the most proximal and the most distal stents 57. For example, if the outer stent graft 10 has three outer stents 25 (not shown), the barbs 57 would be located on the stents 25 closest to the outer proximal end 22 and the outer distal end 23, but not the middle stent 25.

In this embodiment, the inner stent graft 15 does not have anchoring hooks 55, but is secured to the outer stent graft 10 via inner anchoring barbs 58. The anchoring barbs 58 secure the inner stent graft 15 to the outer stent graft 10 by engaging the outer graft material 30 or by engaging the outer stent 25. The cross-sectional view composite stent graft 59 provides an illustration of the anchoring barbs 58 engaging the outer graft material 30.

Although this embodiment describes the anchoring barbs 57 and 58 being used in conjunction, this is not required. For example, an outer stent graft 10 using anchoring stents 45 may be employed in conjunction with an inner stent graft 15 that uses anchoring barbs 58.

FIG. 2a shows a cross-sectional view of the composite stent graft 20 comprising the outer stent graft 10 and the inner stent graft 15. This cross sectional view illustrates a preferred embodiment in which the inner graft material 40 and the outer graft material 30 are in direct contact. In this embodiment, the inner stents 35 are attached to the interior of the inner graft material 40 and the outer stents 25 are attached to the exterior of the outer graft material 30. This configuration typically produces less abrasion than a configuration in which either the inner or outer graft material 40 and 30 is in contact with the inner or outer stent(s) 35 and 25. This cross sectional view also illustrates how the inner anchor hooks 55 serve to attach the inner proximal end 32 of the inner stent graft 15 to the outer proximal end 22 of the outer stent graft 10.

Figure 2B:
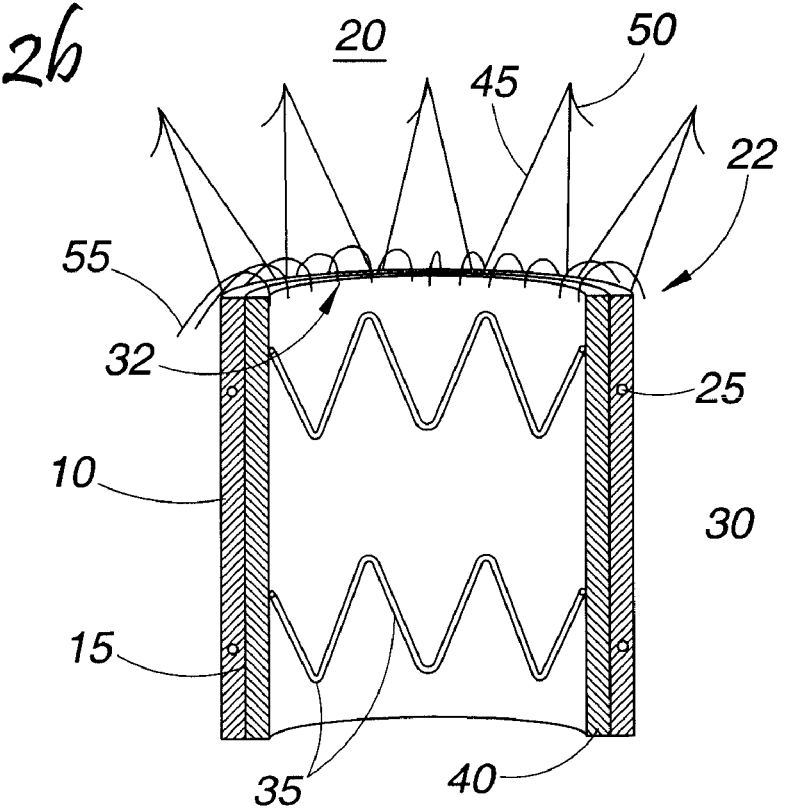
FIG. 2b shows a cross-sectional view of a composite stent graft comprising an outer stent graft and an inner stent graft, where the outer stents are incorporated within the outer graft.

FIG. 2b shows a cross-sectional view of the composite stent graft 21 comprising the outer stent graft 10 and the inner stent graft 15, where the outer stents 25 are incorporated within the outer graft 30. In this embodiment, the inner stent 35 is located on the interior of the inner graft material 40 and the outer stent 25 is incorporated within the outer graft material 30. This provides a smooth surface on the exterior of the outer stent graft 10. In addition, this also provides a smooth surface on the interior of the outer stent graft 10 and the exterior of the inner stent graft 15, which can provide reduced abrasion between the stent grafts 10 and 15 and can also provide a tighter seal between stent grafts 10 and 15.

FIG. 3 shows the outer stent graft 10 and the inner stent graft 15, wherein the outer stent graft 10 and the inner stent graft 15 are deployed within a tertiary stent graft 60. Thus, the outer stent graft 10, the inner stent graft 15 and the tertiary stent graft 60 are combined to provide a tertiary composite stent graft 65. The tertiary stent graft 60 extends between a tertiary proximal end 70 and a tertiary distal end 75 and consists of at least one tertiary stent 80 and a tertiary graft material 85. As with the outer stent graft 10 and the inner stent graft 15, the tertiary stent graft 80 is preferably self-expanding and can be converted from a compressed configuration to an expanded configuration. In this embodiment, a plurality of tertiary anchoring stents 87 are positioned near the tertiary stent proximal end 70. The tertiary anchoring stents 87 are attached to and extend from the tertiary graft material 85. The outer stent 10 is equipped with a plurality of outer anchoring hooks 90 that are attached to and extend from the outer stent proximal end 22, where the outer anchoring hooks 90 are designed to engage the tertiary proximal end 70 and attach the outer stent graft 10 to the tertiary stent graft 60. As previously discussed the inner stent graft 15 is also equipped with the anchoring hooks 55.

As with the stent grafts 10 and 15, the tertiary stent graft 60 should be capable of achieving an enhanced collapsibility relative to a typical stent graft. Thus, the choice of material from which the graft material 85 is made should be based on the material's ability to achieve an enhanced collapsibility when combined with the tertiary stent(s) 80. In addition, the tertiary graft material 85 either consists of or incorporates an ECMM. In one embodiment, the tertiary graft material 85 may comprise a porous biocompatible polymeric material in which a collagenous biomaterial has been dispersed, as is disclosed in U.S. Patent Application Ser. No. 60/558,794 filed Mar. 31, 2004 and U.S. Patent Application Ser. No. 60/558,667 filed Mar. 31, 2004 (which are now U.S. Pat. No. 7,244,444), which are hereby incorporated herein by reference. In another embodiment, the tertiary graft material 85 may consist solely of an ECMM. In any case, the tertiary graft material 85 may be attached to the tertiary stent(s) 80 using any suitable manner, including sutures.

The tertiary composite stent graft 65 may be assembled by first deploying the tertiary stent graft 60 within a body lumen. Once the tertiary stent graft 60 has been secured within the body lumen via the anchoring stents 87, the outer stent graft 10 may be deployed within and attached to the tertiary stent graft 60 via the outer anchoring hooks 90. Next, the inner stent graft 15 may be deployed within the outer stent graft 10 and secured thereto via the inner anchoring hooks 55.

FIG. 4 shows a plurality of telescoping prostheses 104, 109, 114 and 119 combined with a second prosthesis 121 to provide a telescoping composite prosthesis 99. In this embodiment, the telescoping prostheses 104, 109, 114 and 119 comprise a first telescoping outer stent graft 105, a second telescoping outer stent graft 110, a third telescoping outer stent graft 115 and a fourth telescoping outer stent graft 120, respectively. The second prosthesis 121 comprises an inner stent graft 122. In addition, the telescoping composite prosthesis 99 comprises a telescoping outer stent graft 117. Although this example includes four outer stent grafts, any number of outer stent grafts can be employed to provide the telescoping composite stent graft 100. The number of outer stent grafts that are employed will depend on the length of the aneurysm to be treated. For example, it may be desirable to employ a larger number of outer stent grafts in conjunction with a longer aneurysm, such that the length of the aneurysm is spanned by the telescoping composite stent graft 100.

The first outer stent graft 105, which extends between a first proximal end 125 and a first distal end 130, consists of a first graft material 132 and at least one first stent 133. In addition, a plurality of anchoring stents 135 with barbs 140 are located near the first proximal end 125. The anchoring stents 135 are attached to and extend from the first graft material 132, where the anchoring stents 135 are attached to the first graft material 132 in any suitable manner, including sutures. The second outer stent graft 110, the third outer stent graft 115 and the fourth outer stent graft 120 all extend between an outer proximal end 145 and an outer distal end 150. The outer stent grafts 110, 115 and 120 also consist of an outer graft material 152 and at least one outer stent 153. Furthermore, the outer proximal ends 145 of each of the outer stent grafts 110, 115 and 120 are equipped with a plurality of outer anchoring hooks 155. The outer anchoring hooks 155 are attached, using any suitable manner, to the outer graft material 152 of each of the outer stent grafts 110, 115 and 120.

The inner stent graft 122, which extends between an inner proximal end 160 and an inner distal end 165, consists of an inner graft material 170 and at least one inner stent 175. The inner stent graft 122 is also equipped with anchoring hooks 180 that are located near the inner proximal end 160. The anchoring hooks 180 are attached to and extend from the inner graft material 170. In another embodiment, the inner stent graft 122 may also comprise a plurality of telescoping inner stent grafts (not shown), wherein the telescoping inner stent grafts are combined in a similar fashion to the outer stent grafts 105, 110, 115 and 120.

The telescoping composite stent graft 100 is assembled by first deploying the first outer stent graft 105, such that the first outer stent graft 105 is anchored within the body vessel via the anchoring stents 135. Next, the second outer stent graft 110 is deployed such that the anchoring hooks 155 engage the first distal end 130. The third outer stent graft 115 is deployed such that the anchoring hooks 155 engage the outer distal end 150 of the second outer stent graft 110 and the fourth outer stent graft 120 is deployed such that the anchoring hooks 155 engage the outer distal end 150 of the third outer stent graft 115. Once the outer stent grafts 105, 1110, 115 and 120 are deployed and attached, the inner stent graft 122 is deployed within the telescoping outer stent graft 117, such that it extends substantially along the length of these outer stent grafts.

FIG. 5 shows a composite bifurcated prosthesis 199 comprising a first prosthesis 201 and a second prosthesis 208, wherein the composite bifurcated prosthesis 199 is deployed within an aorta 204 with an abdominal aortic aneurysm (AAA) 205. The composite bifurcated prosthesis 199 comprises a composite bifurcated stent graft 200, the first prosthesis comprises an outer bifurcated stent graft 202 and the second prosthesis 208 comprises an inner bifurcated stent graft 203. In this embodiment, the composite bifurcated stent graft 200 extends into both iliac arteries 207. As with the outer stent grafts previously described, the outer stent graft 202 serves to provide the radial force necessary to support the body lumen and seal the composite stent graft 200 against the body lumen. As with the inner stent grafts previously described, the inner stent graft 203 serves to provide a blood impermeable barrier. In addition, the outer stent graft 202 and the inner stent graft 203 are preferably self-expanding and can be converted from compressed configurations to expanded configurations.

The outer stent graft 202 extends between an outer bifurcated proximal end 206 and two outer bifurcated distal ends 207. In this embodiment, the outer stent graft 202 consists of an outer body 215, an outer longer leg 220, and an outer shorter leg 221. Both outer legs 220 and 221 are attached to the outer body 215 at an outer bifurcation 217. The outer body 215 and the outer legs 220 and 221 are composed of an outer graft material 225 and a plurality of outer stents 230, where the outer stents 230 are self-expanding. In addition, the outer stent graft 202 also includes a plurality of proximal anchoring stents 222 and barbs 223 that are located near the outer bifurcated proximal end 206 and are attached to and extend proximally from the outer graft material 225. In a preferred embodiment, the anchoring stents 222 are delivered in a compressed state and are self-expanding. The inner stent graft 203 extends between an inner bifurcated proximal end 212 and two inner bifurcated distal ends 213. In this embodiment, the inner stent graft 203 consists of an inner body 235, and an inner longer leg 240, and an inner shorter leg 241. Both inner legs 240 and 241 are attached to the inner body 235 at an inner bifurcation 237. The inner body 235 and the inner legs 240 and 241 are composed of an inner graft material 245 and a plurality of inner stents 250. In addition, the inner stent graft 203 includes a plurality of anchoring hooks 255 that are located near the inner bifurcated proximal end 212 and are attached to and extend proximally from the inner graft material 245.

The composite bifurcated stent 200 is formed by first deploying the outer stent graft 202, such that the outer body 215 is positioned in the aorta 204 and the outer legs 220 and 221 are each situated in one of the iliac arteries 207. The proximal end 206 of the outer stent graft 202 is secured in place by attaching the anchoring stents 222 by way of the barbs 223 to the aorta 204. In a subsequent step, the inner stent graft 203 is deployed within the outer stent graft 202, such that the inner body 235 is located substantially within the outer body 215 and the inner legs 240 and 241 are located substantially within the outer legs 220 and 221, respectively. The inner stent graft 203 is secured within the outer stent graft 202 by attaching the anchor hooks 255 to the outer bifurcated proximal end 206.

The composite bifurcated stent graft 200 will preferably achieve a blood-tight seal at the outer proximal end 206 and the outer distal ends 210, so that the aneurysm 205 will be excluded. In the particular embodiment shown in FIG. 5, the outer proximal end 206 of the outer stent graft 202 contacts the vascular tissue below the renal arteries 250. The outer distal ends 210 of the outer leg modules 220 and 221 contact the vascular tissue of the iliac arteries 210. This should help to exclude the entire aneurysm 205 and, as a result, the hemodynamic pressures within the aneurysm 205 may be reduced.

FIG. 6 shows a cross-sectional view of a composite prosthesis 261 deployed within a lumen 260 and spanning an aneurismal region 262. In this embodiment, the composite prosthesis 261 comprises the composite stent graft 20, as described above, and is situated within the lumen 260 such that the anchor stents 45 extend proximally from the outer proximal end 22 and the barbs 50 engage the vascular tissue of the lumen 260 proximal to the aneurismal region 262. A seal is preferably achieved between the outer proximal end 22 and the lumen 260, where the seal is proximal to the aneurismal region 262. Another seal is preferably achieved between the outer distal end 23 and the lumen 260, where this second seal is distal to the aneurismal region 262. This will help exclude the entire aneurysmal region 262 and, as a result, the hemodynamic pressures within the aneurismal region 262 may be reduced.

Figure 7:
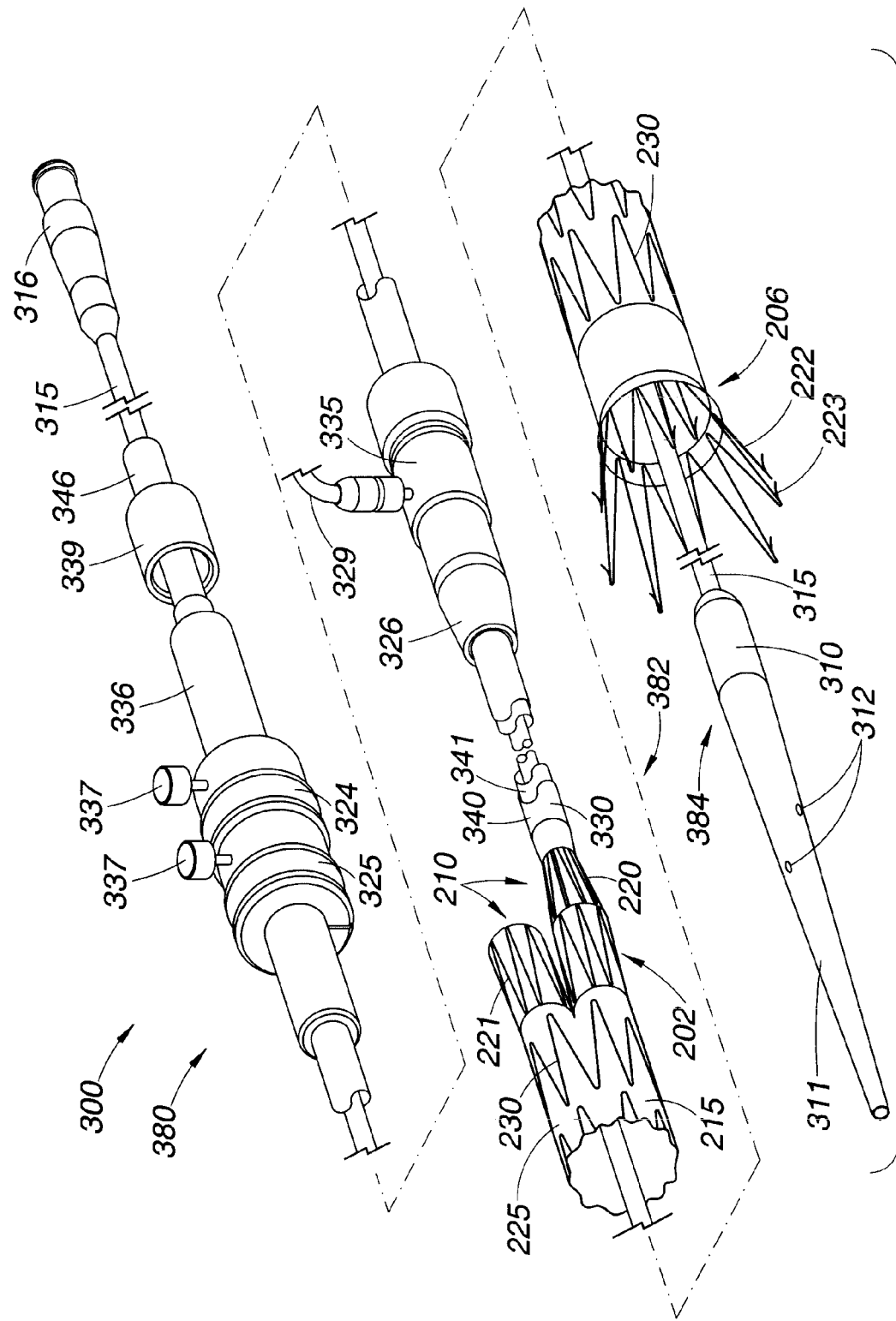
FIG. 7 shows the bifurcated outer stent graft and an endovascular deployment system, also known as an introducer.

FIG. 7 shows the bifurcated outer stent graft 202 and an endovascular deployment system 300, also known as an introducer 300. The deployment system 300 may be used to deploy the outer stent graft 202 and the inner stent graft 203 of the composite bifurcated stent graft 200 within a patient. These items are each described in greater detail in PCT application WO98/53761, which is incorporated herein by reference in its entirety.

The bifurcated outer stent graft 202 has a generally inverted Y-shaped configuration. The outer stent graft 202 includes the outer body 215, the outer longer leg 220 and the outer shorter leg 221. The outer stent graft 202 comprises the bifurcated outer graft material 225 and the plurality of outer stents 230 attached thereto. The self-expanding outer stents 230 cause the outer stent graft 202 to expand following its release from the introducer 300. The outer stent graft 202 also includes the anchoring stents 222 that are attached to and extend proximally from the outer proximal end 206 of the outer graft material 225, where the anchoring stents 222 further comprise the barbs 223. When the anchoring stents 222 are released from the introducer 300, the self-expanding anchoring stents 222 anchor the barbs 223, and thus the outer proximal end 206 of the outer stent graft 202, to the lumen of the patient.

The introducer 300 includes an external manipulation section 380, a distal attachment region 382 and a proximal attachment region 384. The distal attachment region 382 and the proximal attachment region 384 secure the outer distal ends 210 and outer proximal end 206 of the outer stent graft 202, respectively. During the medical procedure to deploy the outer stent graft 202, the distal and proximal attachment regions 382 and 384 will travel through the lumen to a desired deployment site. The external manipulation section 380, which is acted upon by a user to manipulate the introducer 300, remains outside of the patient throughout the procedure.

The proximal attachment region 384 of the introducer 300 includes a cylindrical sleeve 310. The cylindrical sleeve 310 has a long tapered flexible extension 311 extending from its proximal end. The flexible extension 311 has an internal longitudinal aperture (not shown). This longitudinal aperture facilitates advancement of the tapered flexible extension 311 along an insertion wire (not shown). The longitudinal aperture also provides a channel for the introduction of medical reagents. For example, it may be desirable to supply a contrast agent to allow angiography to be performed during placement and deployment phases of the medical procedure.

A thin-walled metal tube 315 is fastened to the extension 311. The thin-walled metal tube 315 is flexible so that the introducer 300 can be advanced along a relatively tortuous vessel, such as a femoral artery, and so that the distal attachment region 382 can be longitudinally and rotationally manipulated. The thin-walled metal tube 315 extends through the introducer 300 to the manipulation section 380, terminating at a connection means 316.

The connection means 316 is adapted to accept a syringe to facilitate the introduction of reagents into the thin-walled metal tube 315. The thin-walled metal tube 315 is in fluid communication with the apertures 312 of the flexible extension 311. Therefore, reagents introduced into connection means 316 will flow to and emanate from the apertures 312.

A plastic tube 341 is coaxial with and radially outside of the thin-walled metal tube 315. The plastic tube 341 is "thick-walled"—its wall is preferably several times thicker than that of the thin-walled metal tube 315. A sheath 330 is coaxial with and radially outside of the plastic tube 341. The thick-walled plastic tube 341 and the sheath 330 extend distally to the manipulation region 380.

During the placement phase of the medical procedure, the outer stent graft 202 is retained in a compressed condition by the sheath 330. The sheath 330 extends distally to a gripping and hemostatic sealing means 335 of the external manipulation section 380. During assembly of the introducer 300, the sheath 330 is advanced over the cylindrical sleeve 310 of the proximal attachment region 384 while the outer stent graft 202 is held in a compressed state by an external force. A distal attachment (retention) section 340 is coupled to the thick-walled plastic tube 341. The distal attachment section 340 retains the distal end 210 of the outer stent graft 202 during the procedure. Likewise, the cylindrical sleeve 310 retains the anchoring stents 222. The distal end 210 of the outer stent graft 202 has a loop (not shown) through which a distal trigger wire (not shown) extends. The distal trigger wire extends through an aperture (not shown) in the distal attachment section 340 into an annular region between the thin-walled tube 315 and the thick-walled tube 341. The distal trigger wire extends through the annular space to the manipulation region 380. The distal trigger wire exits the annular space at a distal wire release mechanism 325.

The external manipulation section 380 includes a hemostatic sealing means 335. The hemostatic sealing means 335 includes a hemostatic seal (not shown) and a side tube 329. The hemostatic sealing means 335 also includes a clamping collar 326 that clamps the sheath 330 to the hemostatic seal, and a silicone seal ring (not shown) that forms a hemostatic seal around the thick-walled plastic tube 341. The side tube 329 facilitates the introduction of medical reagents between the thick-walled tube 341 and the sheath 330.

A proximal portion of the external manipulation section 380 includes a release wire actuation section that has a body 336. The body 336 is mounted onto the thick-walled plastic tube 341. The thin-walled tube 315 passes through the body 336. The distal wire release mechanism 325 and the proximal wire release mechanism 324 are mounted for slidable movement onto the body 336.

The positioning of the proximal and distal wire release mechanisms 324 and 325 is such that the proximal wire release mechanism 324 must be moved before the distal wire release mechanism 325 can be moved. Therefore, the distal end 210 of the outer stent graft 202 cannot be released until the anchoring stents 222 have been released, and the barbs 223 have been anchored to the lumen. Clamping screws 337 prevent inadvertent early release of the outer stent graft 202. A hemostatic seal (not shown) is included so that the release wires can extend out through the body 336 without unnecessary blood loss during the medical procedure.

A distal portion of the external manipulation section 380 includes a pin vise 339. The pin vise 339 is mounted onto the distal end of the body 336. The pin vise 339 has a screw cap 346. When screwed in, vise jaws (not shown) of the pin vise 339 clamp against or engage the thin-walled metal tube 315. When the vise jaws are engaged, the thin-walled tube 315 can only move with the body 336, and hence the thin-walled tube 315 can only move with the thick-walled tube 341. With the screw cap 346 tightened, the entire assembly can be moved together as one piece.

The outer stent graft 202 and the inner stent graft 203 are deployed seriatim. First the bifurcated outer stent graft 202 is deployed, and then, using an identical procedure and another introducer 300, the inner stent graft 203 is deployed. This outer stent graft 202 can be deployed in any method known in the art, preferably the method described in WO98/53761 in which the device is inserted by an introducer 300 via percutaneous entry femoral artery, and then advanced into the desired position over a stiff wire guide using endoluminal interventional techniques. For example, a guide wire (not shown) is first introduced into a femoral artery of the patient and advanced until its tip is beyond the desired deployment region of the outer stent graft 202. At this stage, the introducer assembly 300 is fully assembled, and ready for introduction into the patient. The outer stent graft 202 is retained at one end by the cylindrical sleeve 310 and the other by the distal attachment sections 340, and compressed by the sheath 330. If an aortic aneurysm is to be repaired, the introducer assembly 300 can be inserted through a femoral artery over the guide wire, and positioned by radiographic techniques, which are not discussed here.

Once the introducer assembly 300 is in the desired deployment position, the sheath 330 is withdrawn to just proximal of the distal attachment section 340. This action releases the middle portion of the outer stent graft 202 so that it can expand radially. The anchoring stents 222, however, are still retained within the cylindrical sleeve 310. Also, the outer distal ends 210 of the outer stent graft 202 are still retained within the external sheath 330.

Next, the pin vise 339 is released to allow small movements of the thin-walled tube 315 with respect to the thick-walled tube 341. These movements allow the outer stent graft 202 to be lengthened or shortened or rotated or compressed for accurate placement in the desired location within the lumen. Radiopaque markers (not shown) may be placed along the outer stent graft 202 to assist with placement of the prosthesis.

When the outer proximal end 206 of the outer stent graft 202 is in place, the proximal trigger wire is withdrawn by distal movement of the proximal wire release mechanism 324. The proximal wire release mechanism 324 and the proximal trigger wire can be completely removed by passing the proximal wire release mechanism 324 over the pin vise 339, the screw cap 346, and the connection means 316.

Next, the screw cap 346 of the pin vise 339 is loosened. After this loosening, the thin-walled tube 315 can be pushed in a proximal direction to move the cylindrical sleeve 310 in a proximal direction. When the cylindrical sleeve 310 no longer surrounds the anchoring stents 222, the self-expanding stents 222 expands. When the anchoring stents 222 expand, the barbs 223 grip the walls of the lumen to hold the proximal end of the outer stent graft 202 in place. From this stage on, the outer proximal end 206 of the outer stent graft 202 cannot be moved again.

Once the outer proximal end 206 of the outer stent graft 202 is anchored, the external sheath 330 is withdrawn to distal of the distal attachment section 340. This withdrawal allows the outer shorter leg 221 and the outer longer leg 220 of the outer stent graft 202 to expand. At this point, the outer distal ends 210 of the outer stent graft 202 may still be moved. Consequently, the outer stent graft 202 can still be rotated or lengthened or shortened for accurate positioning. Such positioning of the outer stent graft 202 may ensure that the outer shorter leg 221 extends in the direction of a contralateral artery.

The introducer 300 and deployment method described above can be adapted for implantation in other regions. In addition, a simpler variation of the introducer 300 may be used to introduce the outer and inner stent grafts 10 and 15. This simpler variation of the introducer 300 may be based on the same principles as the introducer 300 described above, but may be less complex.

Other features and aspects of this invention will be appreciated by those skilled in the art upon reading and understanding this specification. Such features, aspects and expected variations and modifications are clearly within the scope of this invention.

It is therefore intended that the foregoing detailed description be regarded as illustrative rather than limiting, and that it be understood that it is the following claims, including all equivalents, that are intended to define the scope of this invention.

The disclosures in U.S. patent application No. 60/731,670, from which this application claims priority, and in the abstract accompanying this applications are incorporated herein by reference.

The invention claimed is:

1. A composite prosthesis comprising:
a first prosthesis comprising a first outer graft for endoluminal placement within a body lumen, and
a second prosthesis comprising an inner stent graft for subsequent endoluminal placement within the first prosthesis,
wherein the first prosthesis comprises a inner abrasion resistant graft having a smooth outer surface, a thickness of about 0.1 mm, is permeable to blood flow, and exerts sufficient radial force to cause the composite prosthesis to securely engage an interior surface of the body lumen at one or both of the composite prosthesis' proximal and distal ends, and
wherein the second prosthesis is entirely impermeable to blood flow and exerts sufficient radial force to expand against and securely engage an inner surface of the first prosthesis in an overlapping relationship forming a composite stent graft.

2. The composite prosthesis of claim 1, wherein the composite stent graft is a bifurcated composite stent graft.

3. The composite prosthesis of claim 1, wherein the first prosthesis comprises an outer stent graft that includes a graft and at least one stent; and the inner stent graft comprises a graft and at least one stent.

4. The composite prosthesis of claim 3, wherein the outer stent graft comprises at least two outer stent grafts in a telescoping relationship with each other.

5. The composite prosthesis of claim 1, wherein the composite stent graft is configured to be deployed within a tertiary stent graft.

6. The composite prosthesis of claim 5, wherein the tertiary stent graft comprises at least one tertiary stent and a tertiary graft, the tertiary graft further comprising an extracellular matrix material.

7. The composite prosthesis of claim 3, wherein the inner stent graft is configured to be deployed substantially within the outer stent graft.

8. The composite prosthesis of claim 3, wherein the outer stent graft and the inner stent graft are adapted for percutaneous introduction into the body lumen.

9. The composite prosthesis of claim 3, further comprising a plurality of anchors at the proximal end of the composite stent graft and attaching the inner stent graft to the outer stent graft by engaging the proximal end of the outer stent graft.

10. The composite prosthesis of claim 9, wherein the anchors secure the inner stent graft to the outer stent graft by engaging the graft material of the outer stent graft or the stent of the outer stent graft.

11. The composite prosthesis of claim 3, further comprising at least one anchoring stent having at least one barb, wherein the anchoring stent is attached to and extends from the proximal end of the outer stent graft.

12. The composite prosthesis of claim 3, wherein the composite stent graft is bifurcated, the outer stent graft is bifurcated and the inner stent graft is bifurcated.

13. The composite prosthesis of claim 3, wherein at least one stent is attached to the exterior of the outer stent graft and at least one stent is attached to the interior of the inner stent graft.

14. The composite prosthesis of claim 3, comprising at least one stent incorporated into the graft material of the outer stent graft.

15. A method of deploying the composite prosthesis of claim 1 into a body lumen, comprising:
endoluminally deploying the first prosthesis within the body lumen; and
endoluminally deploying the second prosthesis substantially within the first prosthesis;
wherein the first prosthesis exerts sufficient radial force to cause the composite prosthesis to securely engage an interior surface of the body lumen at one or both of the composite prosthesis' proximal and distal ends, and
wherein the second prosthesis exerts sufficient radial force to expand against and securely engage an inner surface of the first prosthesis in an overlapping relationship.

16. The method of claim 15, wherein the first prosthesis is an outer stent graft, the second prosthesis is an inner stent graft and the composite prosthesis is a composite stent graft.

17. The method of claim 16, wherein the first prosthesis comprises at least one anchoring stent having barbs.

18. The method of claim 17, wherein the step of deploying the first prosthesis comprises anchoring the outer stent graft within the body lumen via anchoring stents, wherein at least one anchoring stent engage the interior surface of the body lumen via the barbs.

19. The method of claim 18, wherein the step of deploying the second prosthesis comprises securing the inner stent graft to the outer stent graft via anchoring hooks.

20. The method of claim 16, wherein the first prosthesis comprises at least two outer stent grafts, and wherein the step of deploying the first prosthesis comprises deploying the at least two outer stent grafts in a telescoping relationship with each other.

21. The method of claim 16, wherein the outer stent graft and the inner stent graft are percutaneously introduced into the body lumen.

22. The method of claim 16, further comprising endoluminally deploying a tertiary stent graft comprising at least one tertiary stent and at least one tertiary graft material, wherein the first and second prostheses are deployed fully within the tertiary stent graft to provide a tertiary composite stent graft.

23. The method of claim 22, wherein the step of deploying the tertiary stent graft comprises securing the tertiary stent graft within the body lumen via anchoring stents.

24. The method of claim 23, wherein the first prosthesis comprises outer anchoring hooks and the step of deploying the first prosthesis comprises deploying and attaching the first prosthesis to the tertiary stent graft via the outer anchoring hooks.

25. The method of claim 24, wherein the second prosthesis comprises inner anchoring hooks and the step of deploying the second prosthesis comprises securing the second prosthesis to the first prosthesis via the inner anchoring hooks.

26. A method of treating aortic aneurysm comprising endoluminally deploying the composite prosthesis of claim 3 into a body lumen of a patient suffering from aortic aneurysm, wherein the first prosthesis is deployed substantially within and secured to the interior surface of the body lumen before the second prosthesis is deployed substantially within and secured to the first prosthesis.

* * * * *